US00PP19508P2

(12) United States Plant Patent
van den Top

(10) Patent No.: US PP19,508 P2
(45) Date of Patent: Nov. 25, 2008

(54) *HOSTA* PLANT NAMED 'FRAGRANT QUEEN'

(50) Latin Name: ***Hosta* hybrid**
Varietal Denomination: Fragrant Queen

(76) Inventor: Hendrik Jan van den Top, Wesselseweg 46, 3771 PC Barneveld (NL)

( * ) Notice: Subject to any disclaimer, the term of this patent is extended or adjusted under 35 U.S.C. 154(b) by 0 days.

(21) Appl. No.: 12/012,481

(22) Filed: Jan. 31, 2008

(51) Int. Cl.
*A01H 5/00* (2006.01)

(52) U.S. Cl. ..... Plt./353
(58) Field of Classification Search ..... Plt./353
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Hosta* plant named 'Fragrant Queen', characterized by its broadly spreading foliage with upright flower scapes; green and pale yellow variegated foliage; fragrant pale violet to white-colored flowers that are positioned above the foliage on strong scapes; and good garden performance.

2 Drawing Sheets

Botanical designation: *Hosta* hybrid.
Cultivar denomination: 'Fragrant Queen'.

BACKGROUND OF THE INVENTION

The present invention relates to a new and distinct cultivar of *Hosta*, botanically known as *Hosta* hybrid and hereinafter referred to by the name 'Fragrant Queen'.

The new *Hosta* is a naturally-occurring whole plant mutation of the *Hosta* hybrid cultivar Fragrant King, not patented. The new *Hosta* was discovered and selected by the Inventor in a controlled greenhouse environment in Barneveld, The Netherlands in August, 2005.

Asexual reproduction of the new *Hosta* by divisions in a controlled environment in Barneveld, The Netherlands since the spring of 2006, has shown that the unique features of this new *Hosta* are stable and reproduced true to type in successive generations.

SUMMARY OF THE INVENTION

The cultivar Fragrant Queen has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fragrant Queen'. These characteristics in combination distinguish 'Fragrant Queen' as a new and distinct cultivar of *Hosta:*

1. Broadly spreading foliage with upright flower scapes.
2. Green and pale yellow variegated foliage.
3. Fragrant pale violet to white-colored flowers that are positioned above the foliage on strong scapes.
4. Good garden performance.

Plants of the new *Hosta* differ from plants of the parent, the cultivar Fragrant King, primarily in leaf coloration as leaves of plants of the new *Hosta* have a broader pale yellow-colored edge than leaves of plants of the cultivar Fragrant King. In addition, leaves of plants of the new *Hosta* are thicker than leaves of plants of the cultivar Fragrant King.

Plants of the new *Hosta* can be compared to plants of the cultivar Sweet Innocence, not patented. In side-by-side comparisons conducted in Barneveld, The Netherlands, plants of the new *Hosta* and the cultivar Sweet Innocence differed primarily in leaf coloration as plants of the cultivar Sweet Innocence had light green and pale yellow variegated foliage.

BRIEF DESCRIPTION OF THE PHOTOGRAPHS

The accompanying colored photographs illustrate the overall appearance of the new *Hosta*, showing the colors as true as it is reasonably possible to obtain in colored reproductions of this type. Colors in the photographs may differ slightly from the color values cited in the detailed botanical description which accurately describe the colors of the new *Hosta.*

The photograph on the first sheet comprises a side perspective view of a typical flowering plant of 'Fragrant Queen' grown in a container.

The photograph at the top of the second sheet is a close-up view of the upper surfaces of typical developing (left) and fully expanded (right) leaves of 'Fragrant Queen'.

The photograph at the bottom of the second sheet is a close-up view of the lower surfaces of typical developing (left) and fully expanded (right) leaves of 'Fragrant Queen'.

DETAILED BOTANICAL DESCRIPTION

The aforementioned photographs and following observations, measurements and values describe plants grown in containers in Barneveld, The Netherlands, under commercial practice during the late summer in an outdoor nursery with day temperatures ranging from 14° C. to 35° C. and night temperatures ranging from 5° C. to 18° C. Plants had been growing for about 14 months when the photographs and description were taken. In the following description, color references are made to The Royal Horticultural Society Colour Chart, 2001 Edition, except where general terms of ordinary dictionary significance are used.

Botanical classification: *Hosta* hybrid cultivar Fragrant Queen.

Parentage: Naturally-occurring whole plant mutation of the *Hosta* hybrid cultivar Fragrant King, not patented.

Propagation:

*Type.*—By divisions.

*Root description.*—Thick, fibrous; creamy white in color.

*Rooting habit.*—Moderate branching.

Plant description:

*Plant form/habit.*—Herbaceous flowering perennial plant. Mounded plant form with broadly spreading foliage with upright flower scapes. Flowering stems and leaves basal; vigorous growth habit. Pale violet to white-colored flowers are positioned above the foliage on strong scapes.

*Growth rate.*—Fast; about one year are required to produce fully-grown flowering plants.

*Plant height* (*soil level to top of foliar plane*).—About 20 cm to 25 cm.

*Plant height* (*soil level to top of inflorescences*).—About 70 cm.

*Plant width* (*spread*).—About 60 cm.

Foliage description:

*Arrangement/form.*—Leaves basal, simple, generally symmetrical and long-persisting.

*Leaf length.*—About 15 cm to 20 cm.

*Leaf width.*—About 12 cm to 15 cm.

*Shape.*—Cordate.

*Apex.*—Cuspidate.

*Base.*—Cordate.

*Margin.*—Entire.

*Texture, upper and lower surfaces.*—Smooth, glabrous; thick and leathery; moderately rugose.

*Venation pattern.*—Pinnate, arcuate.

*Color.*—Developing leaves, upper surface: Center, 137A to 137C; towards the margins, close to 151C to 151D. Developing leaves, lower surface: Center, more green than 191A; towards the margins, more yellow than 145B. Fully expanded leaves, upper surface: Center, random sectors of 137A, 137B or 137C; towards the margins, close to 150D; venation, similar to lamina. Fully expanded leaves, lower surface: Center, between 191A and 137C; towards the margins, more green than 11D; venation, similar to lamina.

*Petiole length.*—About 12 cm to 20 cm.

*Petiole diameter.*—About 1.2 mm to 1.6 mm.

*Petiole texture, upper and lower surfaces.*—Smooth, glabrous.

*Petiole color, upper surface.*—Close to 137A; towards the margins, 150D.

*Petiole color, lower surface.*—Close to 144B; towards the margins, 150D.

Flower description:

*Flower type/habit.*—Numerous single campanulate flowers with fused perianth arranged on terminal racemes; flowers face outward or slightly downward. Panicles roughly conical in shape. Freely flowering habit with about 15 flowers developing per inflorescence.

*Fragrance.*—Strongly fragrant; sweet, pleasant.

*Natural flowering season.*—Recurrent flowering from summer to early autumn in The Netherlands.

*Postproduction longevity.*—Flowers last about one week on the plant. Flowers not persistent.

*Flower bud.*—Height: About 2 cm to 5 cm. Diameter: About 7 mm to 13 mm. Shape: Elliptic. Color: Close to 144A.

*Inflorescence height.*—About 12 cm to 16 cm.

*Inflorescence diameter.*—About 16 cm to 18 cm.

*Flower diameter.*—About 8 cm.

*Flower depth.*—About 8 cm.

*Perianth.*—Arrangement: Three interior tepals arranged in a single whorl surrounded by an outer whorl of three exterior tepals. Tepal length: About 3.5 cm to 4 cm. Tepal width: About 1.8 cm to 2.4 cm. Tepal shape: Ovate. Tepal apex: Acute. Tepal margin: Entire. Tepal texture, upper and lower surfaces: Smooth, glabrous; satiny. Tepal color: Developing petals, upper and lower surfaces: Close to 85D. Fully expanded petals, upper surface: 85D; towards the base and margin, close to 155D; with development, color becoming closer to 155D. Fully expanded petals, lower surface: Close to 85D.

*Flower bracts.*—Quantity: One per flower at the base of the pedicel. Length: About 1.5 cm. Width: About 5 mm. Shape: Ovate. Apex: Acute. Base: Cuneate. Margin: Entire. Texture, upper and lower surfaces: Smooth, glabrous. Color, upper and lower surfaces: Towards the base, close to 144D; towards the apex, 144A; towards the margins, 11C.

*Peduncles* (*scapes*).—Length: About 60 cm to 70 cm. Diameter: About 6 mm to 8 mm. Angle: Erect. Strength: Strong. Texture: Smooth, glabrous. Color: Close to 191A.

*Pedicels.*—Length: About 1 cm to 1.2 cm. Diameter: About 3 mm. Strength: Strong. Texture: Smooth, glabrous. Color: Close to 191A.

*Reproductive organs.*—Stamens: Quantity per flower: Typically six; anthers dorsifixed. Filament length: About 6.5 cm. Filament color: Towards the base, close to 145C; towards the apex, close to 155D. Anther shape: Narrowly oblong. Anther length: About 6 mm. Anther color: Close to 199B to 199C. Pollen amount: Moderate. Pollen color: Close to 9A. Pistils: Quantity per flower: One. Stigma shape: Lobed. Stigma color: Close to 155D. Style length: About 6 cm. Style color: Close to 155D. Ovary length: About 1.2 cm. Ovary color: Close to 145A.

*Seed/fruit.*—Seed and fruit development have not been observed.

Disease/pest resistance: Plants of the new *Hosta* have not been noted to be resistant to pathogens and pests common to *Hosta*.

Garden performance: Plants of the new *Hosta* have been observed to have good garden performance and tolerate rain, wind and high temperatures of about 35° C. Plants of the new *Hosta* have been observed to be hardy to USDA Zone 5.

It is claimed:

1. A new and distinct *Hosta* plant named 'Fragrant Queen' as illustrated and described.

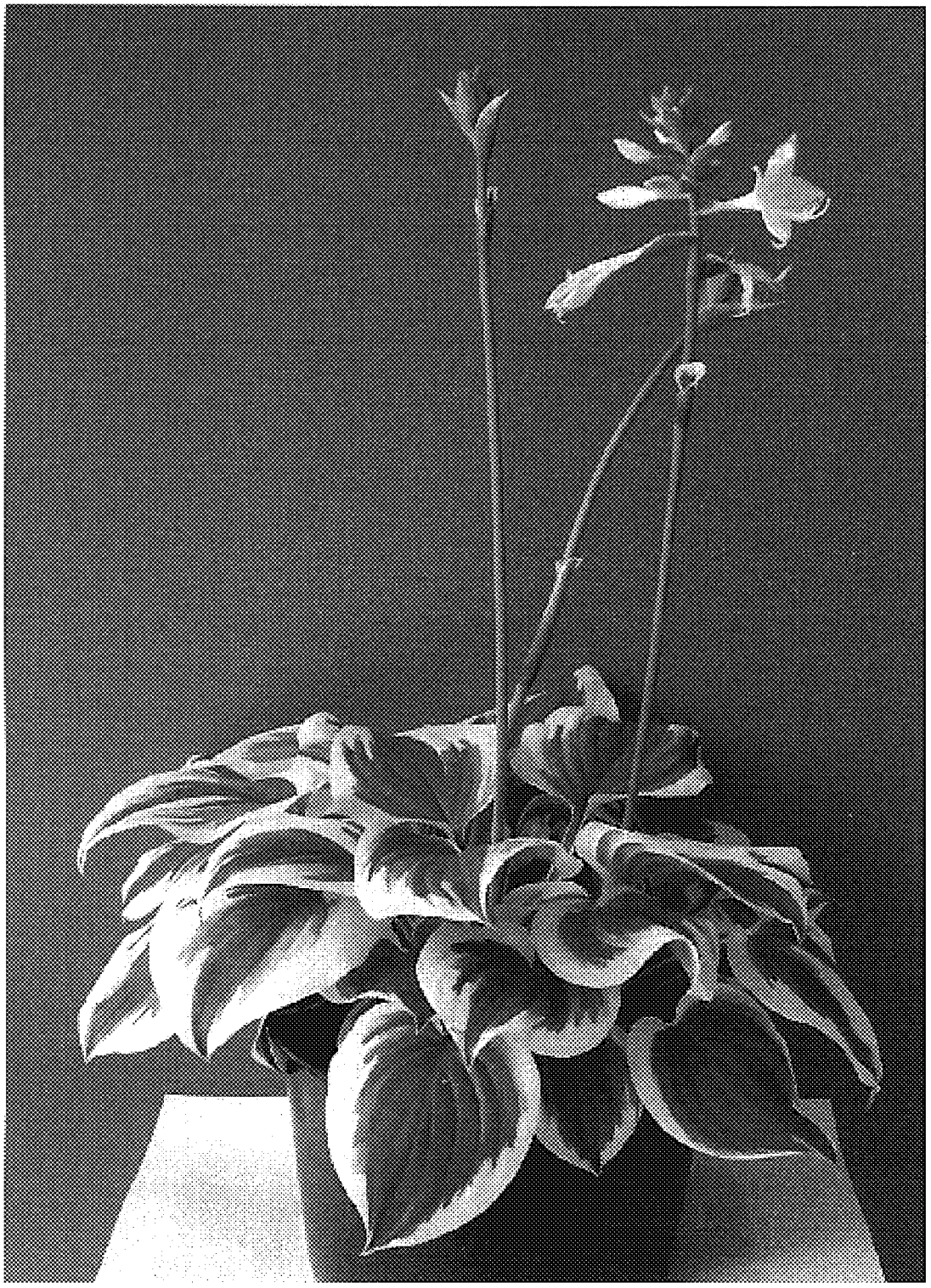

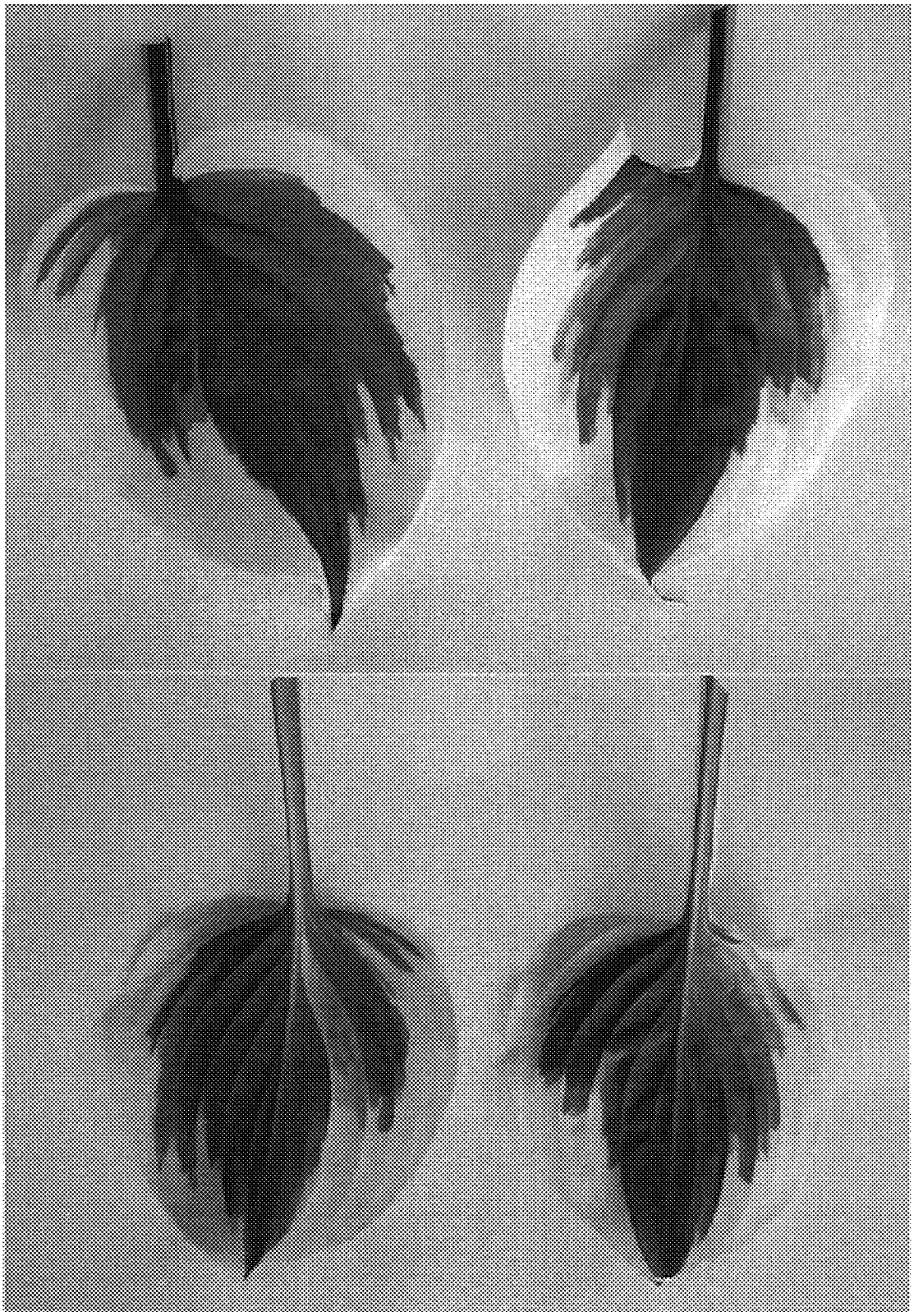

* * * * *